United States Patent
Gåserød et al.

(10) Patent No.: US 7,893,038 B2
(45) Date of Patent: *Feb. 22, 2011

(54) ORAL IMMUNOSTIMULATION OF MAMMALS BIRDS AND REPTILES FROM (1-4) LINKED β-D-MANNURONIC ACID

(75) Inventors: Olav Gåserød, Steinberg (NO); Arne Dessen, Røyken (NO)

(73) Assignee: FMC Biopolymer AS, Drammen (NO)

( * ) Notice: Subject to any disclaimer, the term of this patent is extended or adjusted under 35 U.S.C. 154(b) by 324 days.

This patent is subject to a terminal disclaimer.

(21) Appl. No.: 10/497,211

(22) PCT Filed: Nov. 29, 2002

(86) PCT No.: PCT/NO02/00456

§ 371 (c)(1),
(2), (4) Date: Dec. 17, 2004

(87) PCT Pub. No.: WO03/045402

PCT Pub. Date: Jun. 5, 2003

(65) Prior Publication Data

US 2005/0080036 A1 Apr. 14, 2005

(30) Foreign Application Priority Data

Nov. 30, 2001 (NO) .................. 20015875

(51) Int. Cl.
*A61K 31/734* (2006.01)
*A61K 31/715* (2006.01)
(52) U.S. Cl. .............. 514/54; 514/23; 536/3; 536/123.1; 536/124
(58) Field of Classification Search ............. 514/54, 514/23; 536/3, 123.1, 124
See application file for complete search history.

(56) References Cited

U.S. PATENT DOCUMENTS

| | | | |
|---|---|---|---|
| 5,169,840 A | * | 12/1992 | Otterlei et al. ............ 514/55 |
| 5,939,289 A | | 8/1999 | Ertesvag et al. |
| 6,121,441 A | | 9/2000 | Simensen et al. |
| 6,312,709 B1 | | 11/2001 | Allen et al. |

FOREIGN PATENT DOCUMENTS

| WO | 9111205 | | 8/1991 |
|---|---|---|---|
| WO | WO 91/11205 | * | 8/1991 |
| WO | 9409124 | | 4/1994 |
| WO | WO 98/51710 | | 11/1998 |
| WO | WO 01/56404 A1 | | 8/2001 |

OTHER PUBLICATIONS

Nishide et al. (Journal of Applied Phycology, 5: 207-211, 1993).*
E.H. Son et al., "Stimulation of various functions in murine peritoneal macrophages by high mannuronic acid-containing alginate (HMA) exposure in vivo", International Immunopharmacology, vol. 1, pp. 147-154, 2001.
Michio Fujihara et al., "The effect of the content of D-mannuronic acid and L-guluronic acid blocks in alginates on antitumor activity", Carbohydrate Research, vol. 224, pp. 343-347, 1992.
O. Halaas et al., "Mannuronan Enhances Survival of Lethally Irradiated Mice and Stimulates Murine Haematopoiesis In Vitro", Scand. J. Immunol., vol. 46, pp. 358-365, 1997.
Helga Ertesvåg et al., "Biosynthesis and applications of alginates", Polymer Degradation and Stability, vol. 59, pp. 85-91, 1998.
Wang Wen-Tao, Zhou Jin-Huang, Xing Shan-Tian, Guan Hua-Shi, Immunomodulating action of marine algae sulfated polysaccharides on normal and immunosuppressed mice; *Chinese Journal of Pharmacology and Toxicology*; Aug. 1994, 8(3), 199-202 (Institute of Pharmacology and Toxicology, Beijing 100850).
Liu Yan, Jiang Xiao-Iu, Lu Qing, Guan Hua-shi; Effects of mannuronate polysaccharide on enzymes of *Penaeus chinensis* related with immune and hemolysis; *Journal of Fisheries of China*, Dec. 2000, 24(6), 549-553 (Fisheries College, Ocean University of Qingdao, Qingdao 266003, China).
Øyvind Skaugrud, Anniken Hagen, Berit Borgensen, and Michael Dornish, Biomedical and Pharmaceutical Applications of Alginate and Chitosan, *Biotechnology and Genetic Engineering Reviews*, 16 (April), 23-40, 1999.
Anniken. Hagen, et al., Pharmacokinetics of Sodium Alginate in Mice, *European Journal of Pharmaceutical Sciences*, 4 (September), Supplement, S100 (1996), P1.040,(Poster Session P1:Sunday Sep. 15).
Terje Espevik, et al., "Application of Alginate Gels in Biotechnology and Biomedicine", Carbohydrates in Europe, pp. 19 to 25.
Journal of Fisheries of China, vol. 24, No. 6, Dec. 2000—"Effects of Mannuronate Polysaccharide on Enzymes of *Penaeus chinensis* Related with Immune and Hemolysis." (Abstract is in English).
Skjermo et al., "Techniques for microbial control in the intensive rearing of marine larvae"; Aquaculture vol. 177 (1999) 333-343.

* cited by examiner

*Primary Examiner*—Shaojia Anna Jiang
*Assistant Examiner*—Michael C Henry
(74) *Attorney, Agent, or Firm*—FMC Corporation (57) ABSTRACT

An oral, immunostimulating material for mammals, birds, and reptiles comprising an immunostimulating amount of an alginate having a M content of at least 40% and an acceptable carriers.

2 Claims, 7 Drawing Sheets

Level of phagocytosis for granulocytes

Fig. 6 Oxidative burst in granulocytes

Fig. 7

Immune Response to HSA vaccination

ORAL IMMUNOSTIMULATION OF MAMMALS BIRDS AND REPTILES FROM (1-4) LINKED β-D-MANNURONIC ACID

FIELD OF THE INVENTION

The present invention is directed to an oral, immunostimulating material for mammals, bird, and reptiles comprising an immunostimulating amount of an alginate having a (1-4) linked β-D-mannuronic acid content of at least 40% and, if necessary or desired, an acceptable carrier. The present invention is also directed to a method for stimulating the immune system of a mammal, bird, or reptile comprising orally administering the inventive material to a mammal, bird, or reptile.

BACKGROUND OF THE INVENTION

Alginates are isolated from marine brown algae. Alginate is also produced in some soil bacteria such as *Azotobacter vinelandii* and *Azotobacter crococcum* and several different *Pseudomonas* sp. Brown alga are however generally the source of commercially available alginates.

Alginates are salts of alginic acid, a linear, hetero polysaccharide consisting of (1-4) linked β-D-mannuromic acid, designated herein as M, and α-L-guluronic acid, designated herein as G. These two uronic acids have the following formulae:

β-D-mannopyranuronate (M)
$^4C_1$ confirmation

α-L-gulopyranuronate (G)
$^1C_4$ conformation

The polymers exist as homopolymer sequences of mannuronic acid, called M-blocks, homopolymer sequences of guluronic acid called G-blocks, and mixed sequences of mannuronic and guluronic acid units, designated MG-blocks or alternating blocks. The following scheme represent an illustration of the structure of alginates:

| MMMMMMM | GGGGGGG | GMGMGMGM | GGGGGGGM |
|---|---|---|---|
| M-block | G-block | MG-block | G-block |

Alginates usually contain all three types of blocks and a block mostly consists of three to thirty monomer units. The distribution of the blocks depends on the type of algae from which the alginate is isolated, as well as on the age and part of the plant, for example alginate from the stem may have a different sequence and block composition to alginate isolated from the leaves. The time of year at which the algae are harvested also affects the block composition and sequence. According to the common knowledge, the highest G-content can be found in the stem of old *L. hyperborea*. The leaf of the same species has a somewhat lower G-content and shorter G-blocks, but the content is still higher than most other species. Commercially available alginates usually have a G-content of 25%-70%.

Alginates are known to be used in foodstuffs and in pharmaceutical, dental, cosmetic and other industrial products. The most common industrial applications are based on their hydrocolloidal and polyelectrolytic nature, which forms the basis for the gel-forming, thickening, stabilizing, swelling and viscosity-providing properties.

Alginates that are rich in M content have also been shown to possess immunostimulating activity useful as vaccine adjutants and wound-healing compositions as described in U.S. Pat. No. 5,169,840. A seaweed supplement for mammals and poultry to enhance immune response is described in U.S. Pat. No. 6,312,709. The well-defined oral immunostimulating material of the present invention, which comprises an immunostimulating amount of alginate having a mannuronic acid content of at least 40%, particularly suited for the methods of the invention, is however not anticipated.

SUMMARY OF THE INVENTION

The present invention is directed to an oral, immunostimulating material for mammals, birds, and reptiles comprising an immunostimulating amount of an alginate having a M content of at least 40% and, if necessary or desired, an acceptable carrier.

The present invention is also directed to a method of stimulating the immune system of a mammal, bird, and reptile comprising orally administering an immunostimulating amount of an immunostimulating ingestible material to said mammal, bird and reptile, wherein said material comprises an alginate having a M content of at least 40% and, if necessary or desired, an acceptable carrier.

BRIEF DESCRIPTION OF THE FIGURES

The following abbreviations are used in the figures; *Durvillea* water extract=DWE, *Durvillea* standard extract=Std.DA and *Lessonia* standard extract=Std.LN.

DETAILED DESCRIPTION OF THE INVENTION

Alginates having an M content of at least 40% are utilized as oral immunostimulators in the present invention for mammals, birds, and reptiles. More specifically, alginates having an M content of 50% to 70% (such as derived from *Lessonia, Durvillea*, and *Laminaria*); 70% to 80% (such as derived from *Durvillea*) and 80% to 99.9% (such as derived from bacteria and water extracts of alginates like *Durvillea* as prepared, for example, in accordance with the examples below) may be used. These alginates stimulate the immune response of mammals, birds, and reptiles against disease or trauma caused by cellular attack by foreign bodies and physical injury of cells. Included among foreign bodies are microorganisms, particulate matter, chemical agents and the like. Included among physical injuries are mechanical wounds such as abrasions, lacertions, contusions, wounds and the like.

The oral immunostimulating material and method of the present invention utilize an immunostimulating amount of the alginate having an M content of at least 40%. The immunostimulating amount can vary depending on the subject that is to ingest the immunostimulating material and the level of the immunostimulation that is needed.

The oral immunostimulating material containing the alginate having an M content of at least 40% may be pharmaceutical, veterinary or nutraceutical solid dosage forms such as tablets, caplets, capsules, etc, or as a powder or liquid formulation. It may also be any type of solid or liquid food for mammalian, avian, or reptilian consumption such as pet food. It may also be a solid, semi-solid or liquid nutritional supplement such as food bars, drinks, etc.

Acceptable carriers can be any of those conventionally used in pharmaceutical, veterinary and nutraceutical liquid or solid dosage forms, liquid, solid and semi-solid foods and liquid and solid nutritional supplements.

It has also been found, as demonstrated below in the Examples, that the immunostimulating activity of the alginates of the invention stimulate the weight gain for a mammal (as demonstrated below in pigs (see FIG. 1)) ingesting the alginate as compared to a control. This aspect is particularly useful and desirable when such alginates are orally given to young mammals. As such, the present invention is also directed to a method for stimulating weight gain in mammals, birds and reptiles through immunostimulation comprising orally administering an immunostimulating amount of an immunostimulating material to the mammal, bird, or reptile, wherein the material comprises an alginate having a M content of at least 40% and, if necessary or desired, an acceptable carrier. More specifically, this method also comprises administration of an alginate having an M content of 50% to 70%, 70% to 80% or 80% to 99.9%. The immunostimulating material may be any of those set forth above.

The oral immunostimulating material of this invention can contain alginate having an M content of at least 40% that is synthetically derived or isolated from either alginate-producing bacterial species or seaweed sources.

Alginates having an M content of at least 40% can be obtained from seaweeds by many processes known in the art. The starting material of the alginate having the required M content is algae or seaweed, in particular, brown algae which is generally treated with formaldehyde in order to fixate the phenols and preserve the algae. Further, the algae can be washed with acid to remove the highly viscous laminaran and fucoglycans. Preferably, they can also be treated with alkali to reduce the content of pyrogens. It is understood that the algae can be pre-treated in any known manner. Commercially available alginates, most preferably, dried and milled algae of the species *Durvillea* can be used, but also fresh, whole or unmilled algae from *Durvillea, Laminaria, Lessonia, Ecklonia, Macrocystis*, or *Ascophyllum* are suitable as starting materials.

Processes for producing such alginates are set forth, for example, by Green in U.S. Pat. No. 2,036,934 and Le Gloahec in U.S. Pat. No. 2,128,551 and such processes are incorporated herein by reference. Other methods for obtaining alginates useful in the invention are provided hereinbelow in the examples. For example, alginates of the invention may also be prepared using a water extraction process by mixing an alginate source having a high M content with water in a ratio of 1:3 to 1:20 in a swelling step where the pH is kept above about 2.3 at a temperature above 20° C. for at least 30 minutes, and isolating the solubilised alginate fraction from the solid material by filtration. An alginate having the required M content can be recovered from the solution by precipitation with acid, salt or alcohol.

The Examples set out below include representative examples of aspects of the present invention. The Examples are not meant to limit the scope of the invention but rather serve exemplary purposes. Unless indicated otherwise, all parts, percentages and the like are by weight.

EXAMPLE 1

Starting raw material from different *Durvillea* species; *D. potatorum* (milled), sample 0.1, and *D. antarctica* (not milled), sample 2, were added water in the amounts set forth in the table below, and stirred by hand from time to time, at a temperature of 55° C. for 3.5 hours. After storage at ambient temperature over the night, the algae were extracted a second time at 55° C. for 1 hour, then 2.5 ml formaldehyde was added and the extraction continued for 1 hour.

| Pre-extraction step | | | | | |
| --- | --- | --- | --- | --- | --- |
| Sample | Weight [gram] | Water [ml] | Time [hours] | Temperature [° C.] | Formaldehyde [ml] | pH |
| 1 | 50.0 | 500 | 5.5 | 55 | 2.5 | 5.9 |
| 2 | 40.0 | 500 | 5.5 | 55 | 2.5 | 6.9 |

The suspension was then sieved on a 60-mesh filter and washed 2 times with an excess of water. The solution was then filtrated with filter aids on a vacuum funnel and thereafter on a pre filter of glass filter. The solution was then allowed to cool to 10° C. and was then added NaCl to a 0.5% concentration. Thereafter drops of dilute 5.5 M hydrochloric acid were added by stirring with magnet to a pH 1.8. A white precipitate was formed. The suspension was, after being kept at 10° C. for 30 minutes, sieved on a 120 mesh-filter cloth and pressed by hand resulting in pasty, yellow mass, that turned to fine fiber after pressing. All the acid material was transferred to a 250 ml vessel and added water to 200 ml, before neutralized to pH 7, with solid soda ash under magnetic stirring. The solution was once again filtrated on a 0.8 micron filter membrane of cellulose nitrate. The filtrate was cooled to 10° C. and precipitated with isopropyl alcohol in the ratio 1:1. The fibers formed were washed once with 70 volume % isopropyl alcohol and then a second time with 100 volume % isopropyl alcohol. The fibers were drawn out with a pincer and then freeze-dried. Results are given in the following table.

TABLE

| Sample | Alga | Weight [gram] | Product Yield [gram] | % Alginate (hot water extracted) |
| --- | --- | --- | --- | --- |
| 1 | D. potatorum | 50 | 1.08 | 2.1 |
| 2 | D. antarctica | 40 | 1.59 | 4.0 |

Analysis of product

| Sample | Alga | Intrinsic viscosity dL/g | Molecule weight Dalton/g | % Mannuronic acid NIR model ALGLN2D |
| --- | --- | --- | --- | --- |
| 1 | D. potatorum | 2.7 | 44 009 | 82 |
| 2 | D. antarctica | 7.0 | 118 892 | 88 |

Block-distribution of product measured on NMR 400 Hz

| Sample | Alga | M | G | MM | GG | GM/MG |
| --- | --- | --- | --- | --- | --- | --- |
| 1 | D. potatorum | 85.9 | 14.1 | 76.3 | 4.5 | 9.6 |
| 2 | D. antarctica | 90.9 | 9.1 | 84.8 | 3.0 | 6.1 |

The following table shows yields of M prepared from other seaweed-samples pursuant to the process in this example.

| Alga/Seaweed | Form | Dry Matter % | Yield w/w % | Mannuronic Acid % |
| --- | --- | --- | --- | --- |
| *Ascophyllum nodosum*, spring | Whole, cut | 20 | 0.035 | 90 |
| *Durvillea Antarctica*, Chile, 1996 | Unmilled | 85 | 4 | 91 |
| *Durvillea Antarctica*, Chile, 1996 | Milled | 85 | 6 | 89 |
| *Durvillea Antarctica*, Chile, 1998 | Whole | 85 | 1.3 | 87 |
| *Durvillea Antarctica*, Chile, 2000. | Milled | 85 | 2.5 | 91 |
| *Durvillea potatorum*, Tasmania, 1997 | Milled | 85 | 2.1 | 86 |
| *Lessonia trabeculata*, Chile, 1996 | Milled | 85 | 0.125 | NA |
| *Lessonia nigrescens*, Chile, 1995 | Milled | 85 | — | NA |
| *Laminaria hyperborea*, leaves | Fresh, cut | 18 | — | NA |
| *Saragassum, Tanzania*, August 1991. | Milled | 85 | — | NA |
| *Macrocysts pyrifera*, Chile, 1994 | Milled | 85 | — | NA |
| *Laminaria japonica*, Japan, 1988 | Whole, cut | 85 | 0.2 | NA |
| *Fucus spiralis*, summer, 1994 | Whole, cut | 15 | 0.026 | 91 |

EXAMPLE 2

A sample from August 1996 of *Durvillea antarctica* milled to particles larger than 70 mesh was used as the starting material. 30 gram of dried algae was weighted in a vessel. 100 ml 0.2 M HCl was added and the material was diluted with water to 500 ml. After a few minutes of stirring the pH increased to >2.3 and acid was added to keep pH less than 2.3, (pH 1.8). After 2 minutes 2.5 ml of 0.2M HCl was added. The material swelled very little when the pH was kept constant under pH 2.3 at pH 1.8, compared to swelling with pure water. After swelling for 1 hour, the material was sieved on 60 mesh filtration cloth, pressed by hand and transferred to a vessel. The resulting material was then added 500 ml of water and 50 ml soda ash/sodium hydroxide solution and extracted at 55° C. for 1 hour. The material swelled very quickly and became thick like a paste or pulp. It was stored by ambient temperature until next day. Then the material was further extracted for 1 hour at 55° C. and then milled on a mixer unit Total mass was weighed to 549 gram. 150 gram of material was diluted with 700 gram of water under stirring. The solution was then filtrated on filter paper after addition of filter aids by means of vacuum from water suction. The amount of filtrate was measured to 564 gram and was cooled to 10° C. It was added sodium chloride to 0.5% and pH was adjusted to 1.6 with drops of diluted hydrochloric acid (1:1). A soft precipitate was formed. The material was then sieved on a 120-mesh filtration cloth and pressed carefully by hand. The material was then suspended with water and diluted to a volume of about 200 ml at a temperature of 20° C. The pH of the solution was neutralized to 7 with solid soda ash powder by using a magnetic stirrer. The solution was precipitated with equal parts of isopropyl alcohol solution by stirring with a glass rod. The precipitated fiber was washed once with 70 volume % isopropyl alcohol solution. Then washed again with pure 100 volume % isopropyl alcohol. After sieving and pressing on a 120-mesh filtration cloth, the fibers were drawn out by with pincer and then freeze-dried overnight with vacuum. The yield was weighed to 1.04 gram of alginate, corresponding to 3.6 weight % from the *Durvillea Antarctica* starting material. The content of M was 70% and the block-distribution of the alginate measured by NMR as follows.

| Analysis | M | G | GG | MM | GM/MG |
|---|---|---|---|---|---|
| NIR (algln2d) | 77 | 23 | — | — | — |
| NMR | 78.7 | 21 | 10.9 | 68.3 | 10.4 |

EXAMPLE 3

It is possible to further increase the content of mannuronic acid by addition of salt in the pre-extraction step. 20 gram *Durvillea antarctica* (milled coarse particles>70 mesh) algae from Chile August 1996 was added 500 ml water and a certain amount of NaCl and was extracted under stirring on a Jar test machine, at stirring speed 140 rpm for 2 hours at a temperature of 20° C. The salt was added to a concentration in the solution as set forth in the following table.

TABLE

| Sample | *Durvillea Antarctica* [gram] | Water [ml] | NaCl conc. | Extraction time, [hours] | Remarks |
|---|---|---|---|---|---|
| A | 20 | 500 | 0 | 2 | |
| B | 20 | 500 | 0.2% | 2 | |
| C | 20 | 500 | 0.5% | 2 | |
| D | 20 | 500 | 1.0% | 2 | |
| E | 20 | 500 | 2.0% | 2 | |
| F | 20 | 500 | 3.0% | 2 | |
| G | 20 | 500 | 3.4% | 2 | |
| H | 20 | 500 | — | 2 | Seawater |

The material was then sieved on a 400 mesh filtration cloth and pressed by hand. The sieved solution was weighed and pH measured as given in the following table.

TABLE

| Sample | NaCl conc. | Amount sieved [gram] | pH | Remarks |
|---|---|---|---|---|
| A | 0 | 377 | 6.3 | |
| B | 0.2% | 371 | 6.0 | |
| C | 0.5% | 389 | 6.0 | |
| D | 1.0% | 397 | 5.9 | |
| E | 2.0% | 417 | 5.8 | |
| F | 3.0% | 444 | 5.8 | |
| G | 3.4% | 455 | 5.0 | |
| H | — | 421 | 6.4 | Seawater |

The sieved solution was then filtrated in vacuo (water suction pump) on a funnel with filter paper. The viscosity of the filtrated solution was measured on a glass tube and the results are given in the following table.

TABLE

| Sample | NaCl conc. | Amount of filtrate [gram] | Time Measured, [seconds] | Viscosity calculated [cps] |
|---|---|---|---|---|
| A | 0 | 277 | 18.7 | 11.6 |
| B | 0.2% | 286 | 16.0 | 9.9 |
| C | 0.5% | 319 | 13.8 | 8.6 |
| D | 1.0% | 330 | 12.2 | 7.6 |
| E | 2.0% | 408 | 7.5 | 4.7 |
| F | 3.0% | 438 | 4.9 | 3.0 |
| G | 3.4% | 445 | — | 2.6 |
| H | — | 402 | — | 2.9 |

The filtrate was cooled to below 15° C. and each of the samples were added drops of 5.5 M hydrochloric acid until the pH reached 1.8-2.0, under stirring with a magnetic stirrer. A fiber shaped precipitate was formed. The precipitate was then sieved on a 400-mesh filtration cloth and pressed by hand. The alginic acid was then diluted with water and neutralized with solid soda ash to pH 6-7 under stirring until completely solved. The solution was then cooled and precipitated with equal parts of isopropyl alcohol. Thereafter washed with 70 volume % isopropyl alcohol, and repeatedly washed with pure 100 volume % isopropyl alcohol. The precipitated fiber was pulled out with a pincer and transferred to a vessel and freeze dried overnight in vacuum. The results are shown in the following table, wherein the amount of yield was calculated assuming that no alginate was lost and that all the alginate is solved in the water added.

TABLE

| Sample | NaCl conc. | Amount alginate precipitated [gram] | Amount alginate [g/l] | % yield 100% | % yield real | M-block. NIR Model ALGLN2D |
|---|---|---|---|---|---|---|
| A | 0 | 1.26 | 3.34 | 8.4 | 6.3 | 88% |
| B | 0.2% | 1.03 | 3.60 | 9.0 | 5.1 | |
| C | 0.5% | 1.1 | 3.48 | 8.7 | 5.6 | |
| D | 1.0% | 1.14 | 3.45 | 8.6 | 5.7 | |
| E | 2.0% | 1.20 | 2.87 | 7.2 | 6.0 | |
| F | 30% | 0.80 | 1.80 | 4.5 | 4.0 | |
| G | 3.4% | 0.54 | 1.21 | 3.0 | 2.7 | 91.8% |
| H | Seawater | 0.53 | 1.32 | 3.3 | 2.7 | 95.8% |

EXAMPLE 4

The content of mannuronic acid in the separate fraction was further increased by addition of CaCl$_2$. The starting material was *D. antarctica* from Chile that was milled to coarse particles>70 mesh. The amounts and conditions of the pre-extraction step are set out in the following table. The pre-extraction was carried out under stirring on Jar tester with about 140 rpm.

TABLE

| Sample | Weight [gram] | Water [ml] | Time [hours] | Temperature [° C.] | pH | Calcium chloride [N] |
|---|---|---|---|---|---|---|
| A | 20.0 | 500 | 2 | 25 | 6.08 | 0.01 |
| B | 20.0 | 500 | 2 | 25 | 5.85 | 0.1 |
| C | 20.0 | 498 | 2 | 25 | 5.8 | 0.03 |
| D | 20.0 | 496 | 2 | 25 | 5.7 | 0.06 |

The material was then sieved on a 400-mesh filter and pressed by hand. The solution was then heated to about 30° C. and filtrated with paper on a vacuum suction flask.

TABLE

| Sample | Calcium chloride [N] | Sieved sol. 400 mesh [gram] | Filtrated solution [gram] |
|---|---|---|---|
| A | 0.01 | 404 | 397 |
| B | 0.1 | 462 | 457 |
| C | 0.03 | 423 | 398 |
| D | 0.06 | 440 | 420 |

The solution was then cooled to 10° C. and added sodium chloride to 0.5%. Then drops of 5.5 M HCl was added, with carefully magnetic stirring until pH 1.8. A white precipitate was formed. The material suspension was then stored for 30 minutes and sieved on 400-mesh filtration cloth and pressed carefully by hand. The material was a pasty yellow mass, which turned to fine bright fibers after pressing. The acid material was then transferred to a 250 ml vessel and added water to 200 ml and then neutralized pH 7 with solid soda ash under magnetic stirring. The filtrate was then cooled to 10° C. and precipitated on stirring with 100 volume % isopropyl alcohol in a ratio 1:1. Large fibers were precipitated. The fibers were washed twice with 70 volume % isopropyl alcohol and finally with 100 volume % isopropyl alcohol. The fibers were then pulled out with a pincer, and thereafter freeze-dried overnight under vacuum. The results are given in tables 9 and 10 which show the yields and the increase in content of mannuronic acid in the alginate with more than 80% M from maximum 91%, when salt not was added, to a maximum of 95%, when salt was added to the pre-extraction step.

TABLE

| Sample | Calcium Chloride [N] | Yield alginate [gram] | Yield Alginate [g/l] | Yield 100% % | Yield real % |
|---|---|---|---|---|---|
| A | 0.01 | 1.29 | 3.19 | 8.0 | 6.5 |
| B | 0.1 | — | 0 | 0 | 0 |
| C | 0.03 | 0.52 | 1.31 | 3.28 | 2.6 |
| D | 0.06 | 0.19 | 0.45 | 0.33 | 0.9 |

TABLE

| Sample | Calcium Chloride [N] | % Mannuronic acid NIR model LND 2 | % M NMR | % G NMR | % MM NMR | % GM/ MG NMR | % GG NMR |
|---|---|---|---|---|---|---|---|
| A | 0.01 | 98.7 | 89.0 | 11.0 | 82.0 | 8.0 | 3.0 |
| B | 0.1 | — | — | — | — | — | — |
| C | 0.03 | 101.6 | 92.0 | 8.0 | 86.0 | 6.0 | 1.6 |
| D | 0.06 | 102.5 | 95.0 | 5.0 | 90.0 | 5.0 | 0 |
| E | water only | | 88.7 | 11.3 | 80.4 | 8.3 | 3.0 |

EXAMPLE 5

A total of forty eight cross breed [(Norwegian Landrace× Yorkshire)×Norwegian Landrace] 35 to 38 days old weanling pigs from six litters with an average initial weight of 13.07 kg (STD 1.98) were divided into four groups for an experimental feeding study and placed in an environmentally controlled nursery. Initially pigs were housed at four pigs per 2.5 m by 2.5 m pen. After six weeks of feeding, the pigs were transferred to 15 square meter pens with individual feeding stalls with six pigs per pen. Pigs were allowed access to feed and water ad libitum. Pigs were individually weighed on a weekly basis. Pigs were allowed a 4 day preliminary period of adjustment to the pens and the standard commercial weaningly pig feed. The commercial feed (13% moisture content) was fortified with vitamins and minerals required for growth and had a raw protein content of about 18-19%, a digestible protein content of 14-15%, a starch content of 40-50%, and a raw fat content of about 2.6%.

After the initial adjustment to commercial feed, four groups of each twelve pigs were given a different diet for ten weeks. The final two weeks of the study the pigs were all given the commercial feed. Pigs in the control group were fed the standard commercial feed while pigs in the other three groups were fed the same commercial feed which had been blended with 1.25% (w/w) of alginate. The three alginates tested were 1. *Durvillea antarctica* water extract (89% M), 2. *Durvillea antarctica* standard extract (63% M) and 3. *Lessonia nigenscen* standard extract (55% M). These alginate powders as characterized by intrinsic viscosity and $^1$H NMR spectroscopy measurements are further described as follows:

*Durvillea antarctica* standard extract had an intrinsic viscosity of 7.0 g/dl which corresponds to an estimated weight average molecular weight of 210,000 Daltons using the Mark Houwink equation. This *Durvilla* alginate sample had a mole fraction content for mannuronate (M) units of 0.63 and for guluronate (G) units of 0.37. The fractional content of the M to M linkages, F(MM), was 0.44. The fractional content for the G to G linkages, F(GG), was 0.18. The fractional content of the M to G linkage, F(MG), which is equal to the fractional content of the G to M linkage F(GM), was 0.19.

*Durvillea antarctica* water extract or *Durvillea* water extract, obtained by selective precipitation of an alginate fraction having an increased the M content, had an intrinsic viscosity of 4.7 g/dl which corresponds to an estimated weight average molecular weight of 85,000 Daltons using the Mark Houwink equation. This *Durvillea* water extract alginate sample had a mole fraction content for mannuronate (M) units of 0.88 and for guluronate (G) units of 0.12. The fractional content for the M to M linkages, F(MM), was 0.80. The fractional content for the G to G linkages, F(GG), was 0.04. The fraction content of the M to G linkage, F(MG), which is equal to the fractional content of the G to M linkage F(GM), was 0.08.

*Lessonia nigrescens* standard extract had an intrinsic viscosity of 13.4 g/dl which corresponds to an estimated weight average molecular weight of 370,000 Daltons using the Mark Houwink equation. This *Lessonia* alginate sample had a mole fraction content for mannuronate (M) units of 0.55 and for guluronate (G) units of 0.45. The fractional content of the M to M linkages, F(MM), was 0.35. The fractional content for the G to G .linkages, F(GG), was 0.25. The fractional content of the M to G linkage, F(MG), which is equal to the fractional content of the G to M linkage F(GM), was 0.20.

The alginate intrinsic viscosity was determined using the method disclosed in *Alginates as immobilization materials—A study of some molecular and functional properties* (Martinsen, Anita) Thesis; NTH—University of Trondheim, 1990. The weight average molecular weight was estimated based on the intrinsic viscosity data and the Mark Howink equation. The monomer composition and sequential arrangement were analyzed by $^1$H-NMR spectroscopy on a Brucker 400 WM spectrometer as described by Grasdalen et al,, "A NMR studie of composition and sequence of uronate residues in alginate", in Carbohydrate research 1979; 68:23 and H. Grasdalen "High Field $^1$H NMR spectroscopy of alginate: sequential structure and linkage conformation" in *Carbohydrate Research,* 1983; 118:255.

After two weeks of feeding, the pigs were immunized (at 7 weeks of age) and they were given a booster injection four weeks later (at 11 weeks of age). All pigs were immunized intramuscularly with 0.5 ml of a mixture of 0.25 ml Pneurmabort K® (102BY0002, Fort Dodge Laboratories) containing equine herpes virus 1 (EHV) and 0.25 ml Human serum albumin (HSA)(200 µg/ml) (Sigma), subcutaneously with 0.5 ml Prevacun F® (027021E, Hoechst Roussel Vet, Germany) containing influenza virus A/Equi 1, A/Equi 2/M, A/Equi 2/F (EIV) and 1.0 ml Diphteri/Tetanus vaccine® (DT9169a1, SBL Vaccin AB, Stockholm) containing diphtheria toxoid (30 Lf/ml) and tetanus toxoid (7.5 Lf/ml).

Specific antibodies against Human serum albumin (HSA) (Sigma Chemical Industries, USA) and Diphteriae toxoid (DIF) (National Institute of Public Health) were measured by a passive haemagglutination test (Avrameas et al 1969). The lowest dilution tested was 1:8. Sera that showed no inhibition were given a titre of 4 for use in the statistical calculation. The antibody titre values were $log_2$-transformed to normalize the distribution.

Blood samples were collected at two week intervals for serology, haematology, and for functional characterization of phagocytes and lymphocytes. Serum was isolated and stored at −20° C. until processed. Stabilized (heparinized and EDTA) blood samples were collected in the morning and analysed immediately. The blood samples were analysed (Technicon H-1) at the Central Clinical Laboratory at The Norwegian School of Veterinary Science, Oslo. The total leukocyte count (WBC×$10^9$/L), number (×$10^9$/L) of monocytes, neutrophils and eosinophils were measured electronically and the number of lymphocytes and the relative number (%) of lymphocytes, monocytes, neutrophils and eosinophils were estimated. The total erythrocyte counts (RBC×$10^{12}$/L), the mean cell volume (MCV fL) and haemoglobin (HGB g/L) were measured and the hematocrit (HCT L/L) was estimated.

The phagocytic activity of granulocytes in the blood was assayed using Phagotest® (Orpegen Pharma, Heidelberg) following the operator's manual. Heparinized (15 IU/ml) whole blood was mixed and aliquoted (100 µl) on the bottom of a 5 ml vial (Falcon) and incubated 10 minutes on ice before adding 20 µl precooled stabilized and opsonized FITC-labelled *E. coli* suspension (test kit). All vials were shaken and the test samples were incubated for 10 minutes at 37° C. in a water bath, whereas the control samples remained on ice. All samples were then simultaneously placed on ice in order to stop phagocytosis and 100 µl of ice cold Quenching solution was added to each samples and mixed on a vortex mixer. The samples were then added 3 ml Washing solution, mixed and the cells were spun down (250×g, 5 min, 4° C.). The washing procedure were then repeated before adding 200 µl of DNA staining solution The samples were mixed and incubated 10 minutes on ice, and the cells were analysed by flow cytometry (FACScan™, LYSIS™ software) using the blue-green excitation light (488 nm). The percentage of cells having preformed phagocytosis was analysed.

The evaluation of oxidative burst activity was performed by flow cytometry using Phagoburst® (Orpegen Pharma, Heidelberg) following the operator's manual. Heparinized (15 IU/ml) whole blood was mixed and aliquoted (100 µl) on the bottom of a 5 ml vial (Falcon) and incubated 10 minutes on ice before adding 20 µl precooled stabilized and opsonized *E. coli* suspension (test kit). Three control vials were included for each animal tested; one tube was added 20 µl of Washing solution (negative control), one tube was added 20 µl of the chemotactic peptide fMLP working solution ("low control") and one tube was added 20 µl of phorbol 12-myristate 13-acetate (PMA) working solution ("high control"). All vials were mixed and the test samples were incubated for 10 minutes at 37° C. in a water bath. All samples were then added 20 µl of Substrate solution, mixed thoroughly and incubated for another 10 minutes at 37° C. in a water bath. All samples were then simultaneously taken out of the water bath and the whole blood was lysed and fixed with 2 ml prewarmed Lysing solution, mixed and incubated for 20 min at room temperature. The samples were spun down (250×g, 5 min, 4° C.) and washed once by adding 3 ml Washing solution (250×g, 5 min., 4° C.). The supernatant was decanted and 200 µl of DNA staining solution was added, the samples were mixed and incubated 10 minutes on ice (light protected). The cells were analysed by flow cytometry (FACScan™, LYSIS™ software) using the blue-green excitation light (488 nm). The percentage of cells having produced reactive oxygen metabolites was analysed as well as their mean fluorescence intensity.

Figure 1:
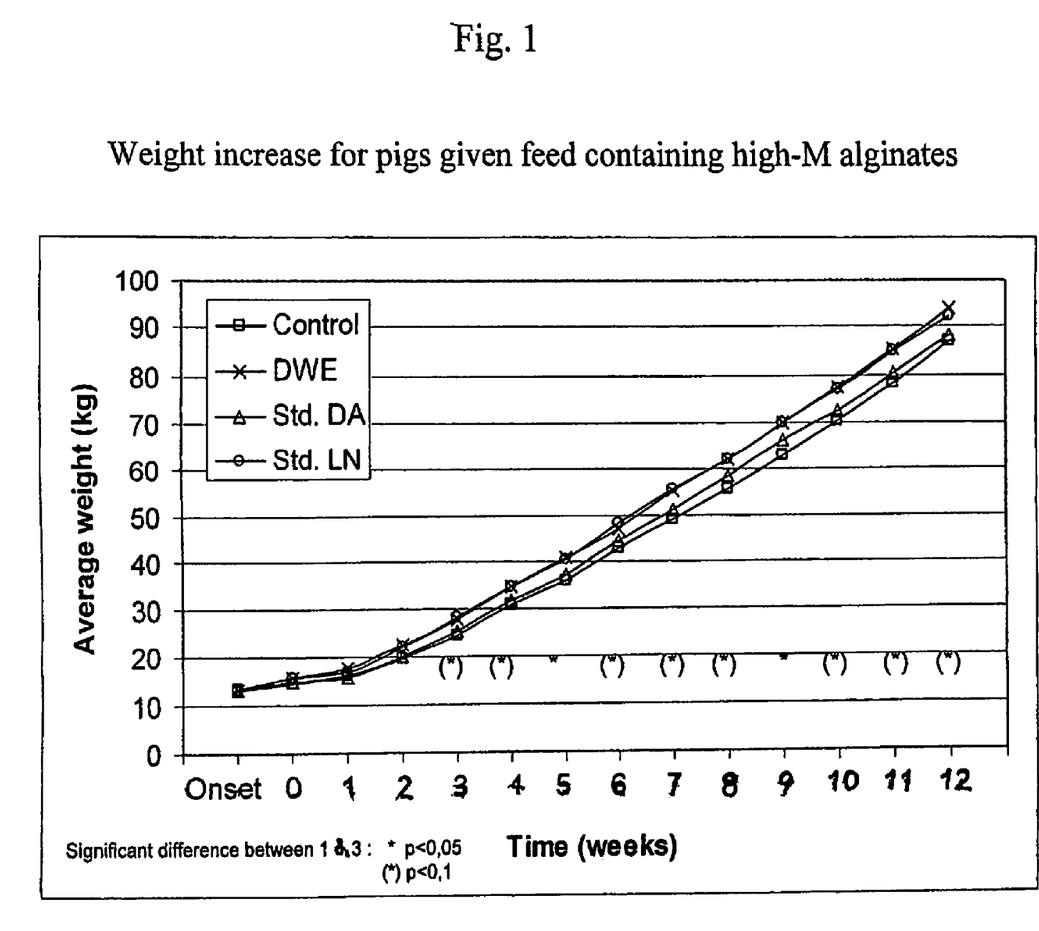
FIG. 1 is a graph showing the weight increase of pigs given feed containing alginates of the invention over a twelve week period.

FIG. 1 shows mean weight for the four groups of pigs as a function of feeding time. A significant weight increase was found for pigs in the *Durvillea* water extract group and *Lessonia* group compared to the control group. The weight difference is deemed statistically significant after week 3, however FIG. 1 shows a trend in weight gain consistent with the *Durvillea* water extract group and the *Lessonia* group increasing in weight more rapidly than the control group after week 1. While the actual weight differential between the *Durvillea* group and the control group is not as dramatic as that seen for the *Durvillea* water extract group and *Lessonia* group, it should be noted that the mean weight of the *Durvillea* group was consistently higher than the control. The individual pigs in the control group had a higher variability in weight compared to individuals in the three groups which had alginate-containing feed which suggests that some individuals in the control group had a reduced immune response since they were less able to cope with trauma and/or stress. The hormone Cortisol in pigs partitions nutrients away from muscle and adipose tissue to allow the animal to cope with disease stress.

Figure 2:
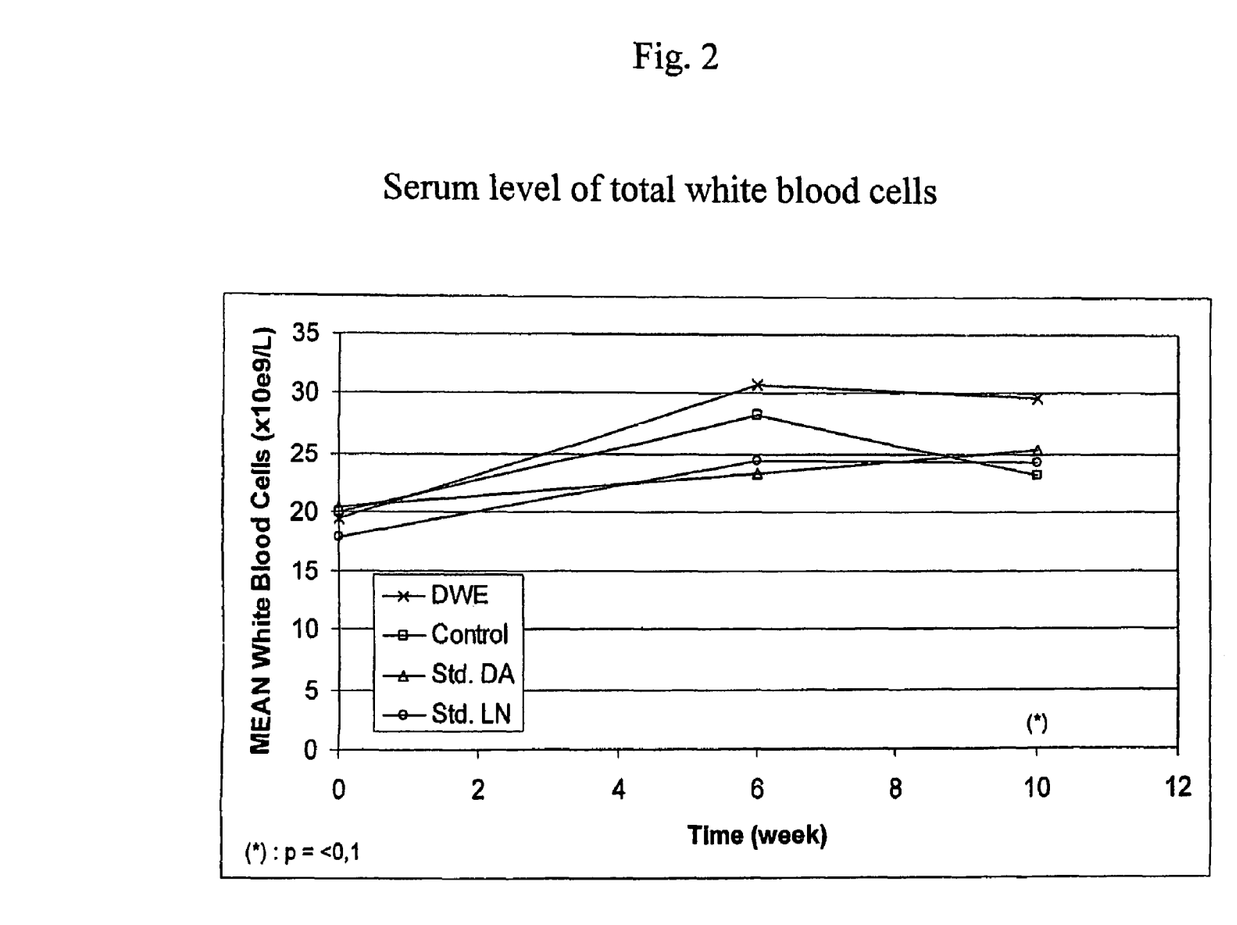
FIG. 2 is a graph showing the serum level of total white blood cells in the pigs tested with alginates of the invention as compared to a control.
Figure 3:
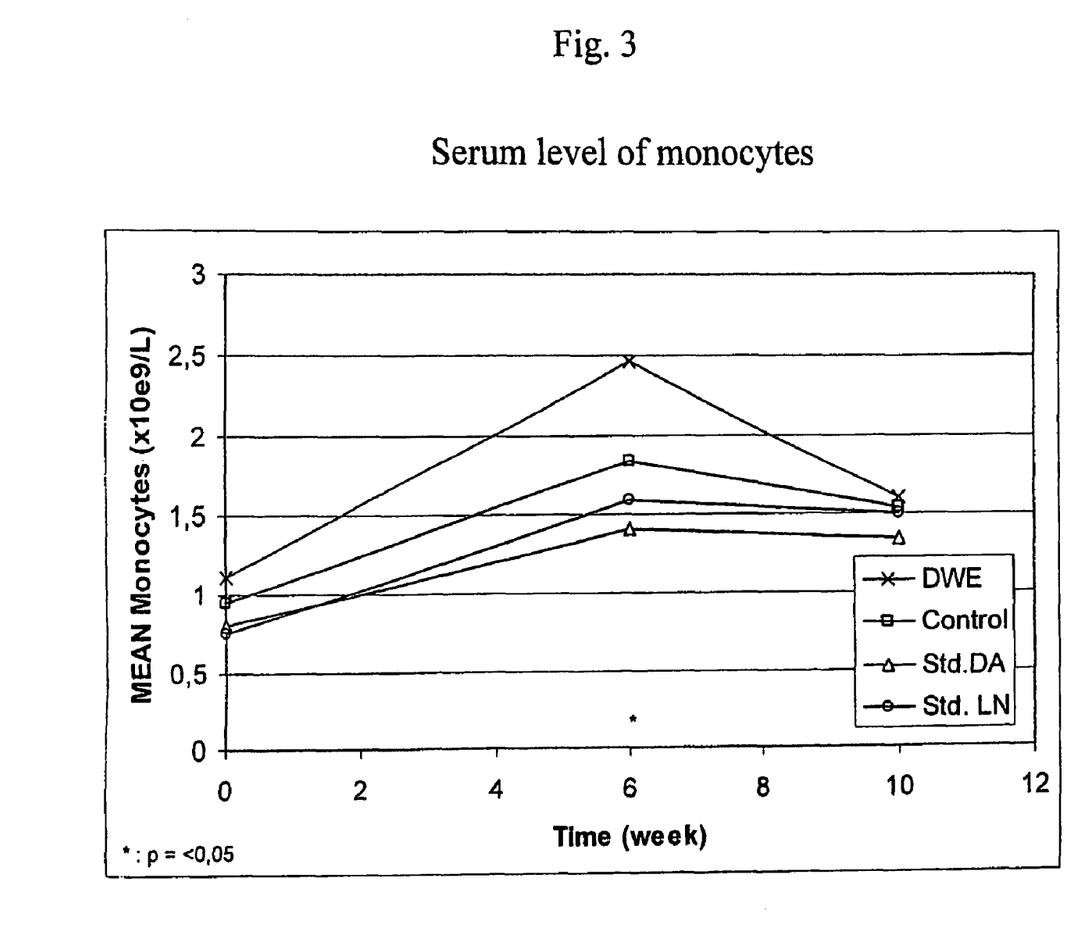
FIG. 3 is a graph showing the serum level of monocytes in the pigs tested with the alginates of the invention as compared to a control.
Figure 4:
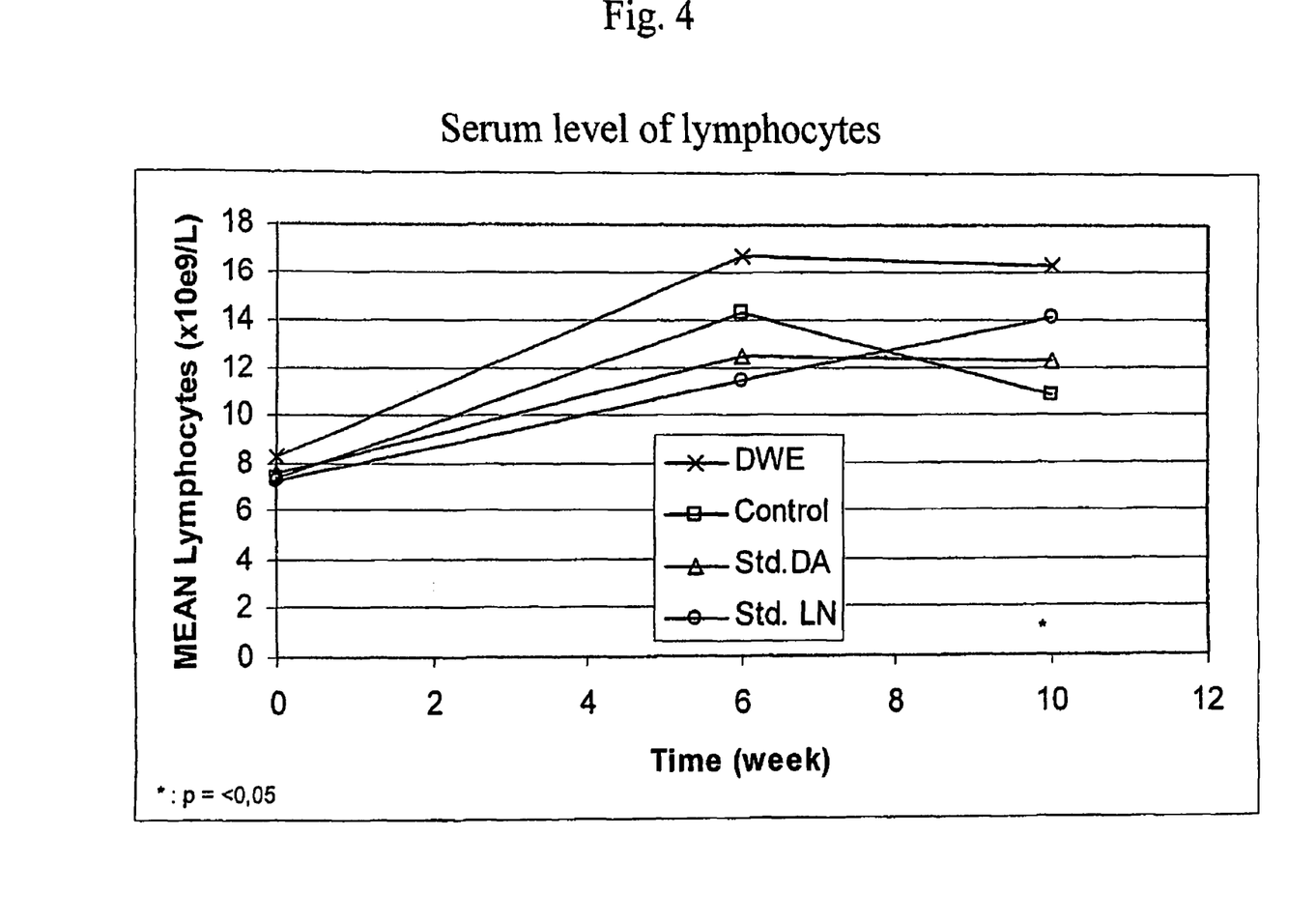
FIG. 4 is a graph showing the serum level of lymphocytes in the pigs tested with the alginates of the invention as compared to a control.
Figure 5:
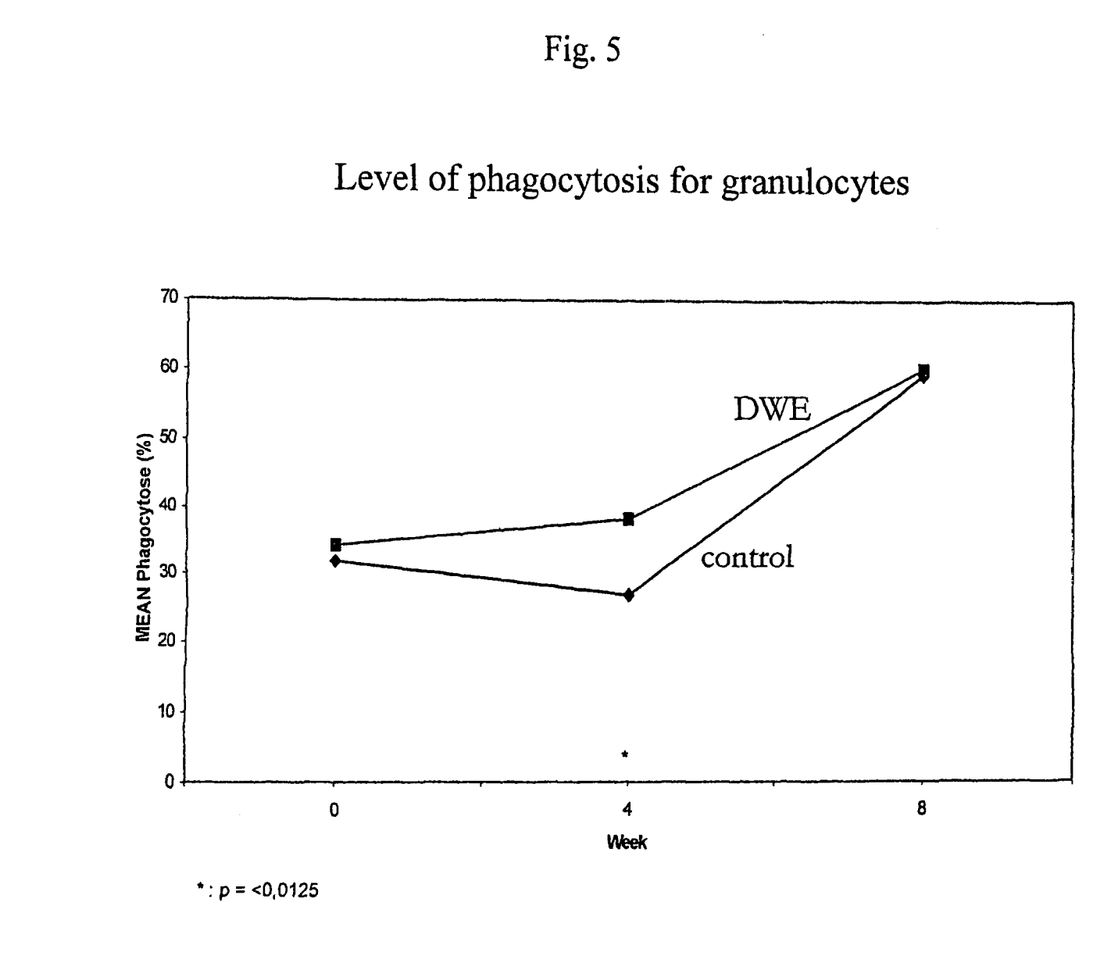
FIG. 5 shows the level of phagocytosis measured using blood from pigs fed *Durvillea* water extract as compared to a control.
Figure 6:
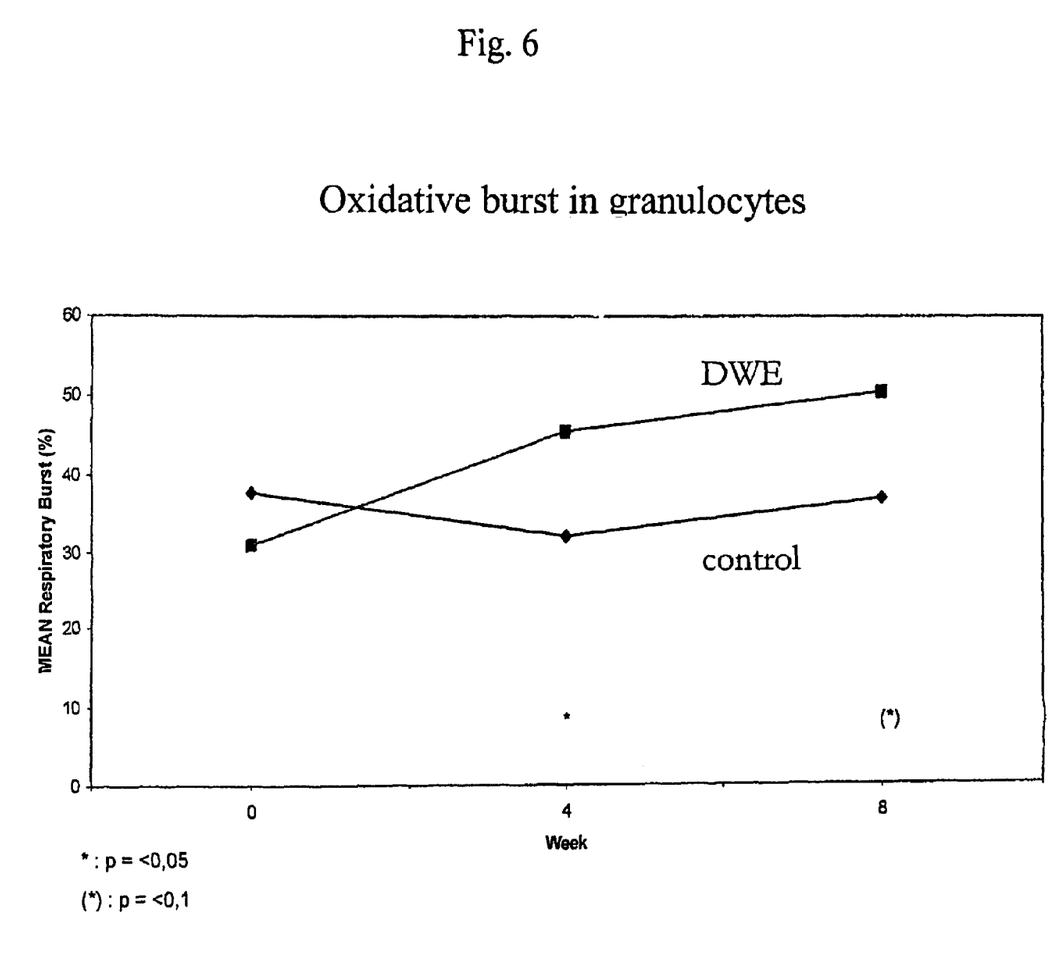
FIG. 6 shows the oxidative burst measured using blood from pigs fed the *Durvillea* water extract as compared to a control.

FIGS. 2 through 4 show data obtained by analyzing the blood for total white blood cells, monocytes and lymphocytes. While not statistically significant, FIG. 2 indicates that the total white blood cells for *Durvillea* water extract group is higher than the control group. The increase white blood cell count observed for the *Durvillea* water extract group is due to significant increases in both monocytes (FIG. 3) and lymphocytes (FIG. 4) after 6 and 10 weeks, respectively, for the *Durvillea* water extract group compared to the control group. The lymphocytes for the *Lessonia* group show a delayed increase (week 10) compared to the *Durvillea* water extract group. The blood taken from the *Durvillea* water extract group (and control group) were also assayed for phagocytic activity, and significant increases were measured for the *Durvillea* water extract group compared to the control group at week 4 as seen in FIG. 5. The oxidative burst data shown in FIG. 6 further supports the higher level phagocytic response for the pigs fed the *Durvillea* water extract compared to the control at both week 4 and week 8. The sustained increased oxidative burst at week 4 and week 8 for the *Durvillea* water extract group compared to the control group is significant since the underlying chemical processes associated with respiratory burst are necessary to kill some types of bacteria and indicates improved effectiveness of phagocytosis.

Figure 7:
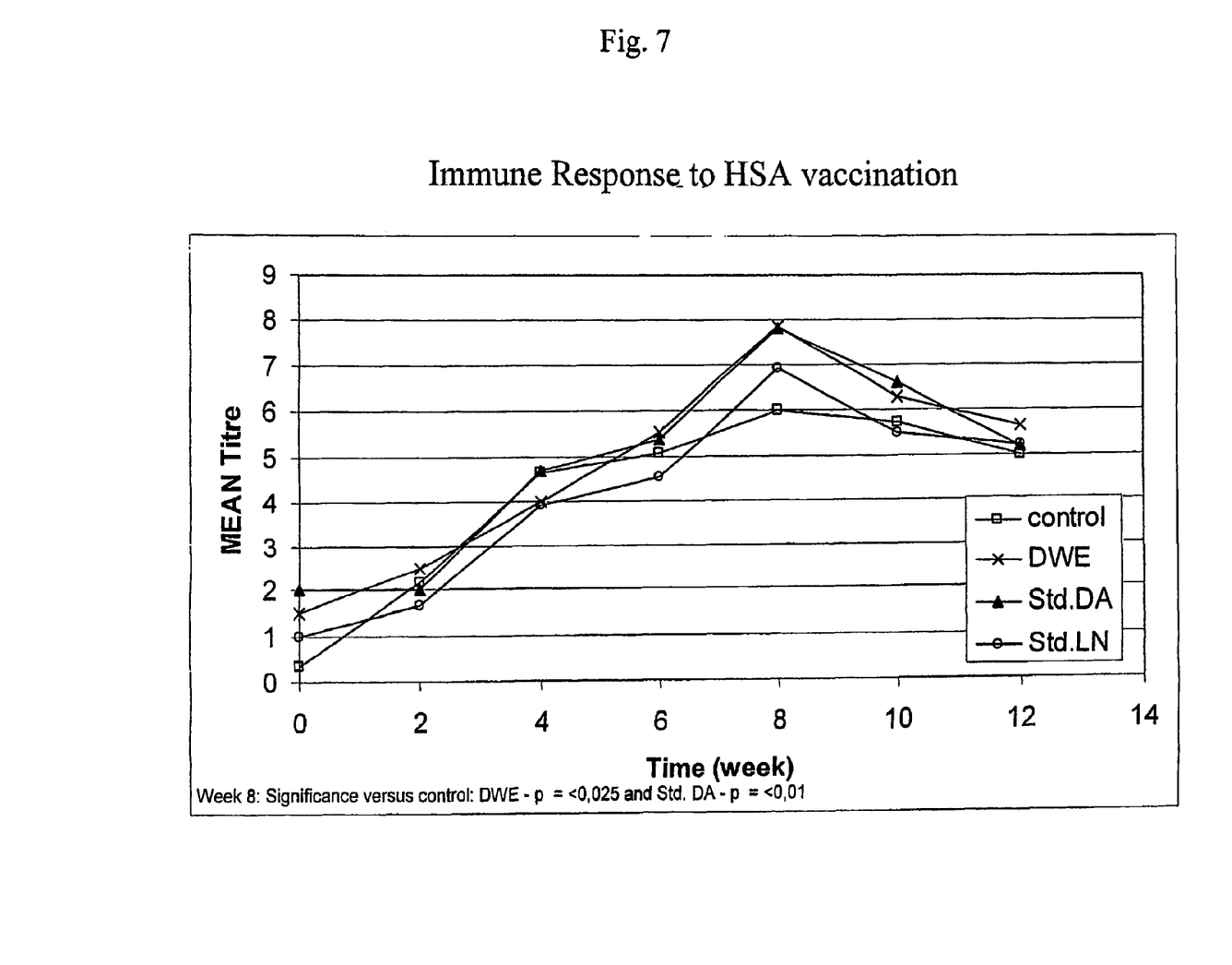
FIG. 7 shows the immune response to an injected Human Serum Albumin experimental vaccine for pigs fed *Durvillea* standard extract, *Durvillea* water extract and *Lessonia* standard extract as compared to a control.

FIG. 7 indicates the immune response to vaccination. The immunoresponse to injection of Human Serum Albumin experimental vaccine (FIG. 7) shows a significant increase at week 8 for the *Durvillea* water extract group and the *Lessonia* group which indicates an improved immune response compared to the control.

We claim:

1. A method of stimulating weight gain in a mammal, a bird, or a reptile comprising orally administering to said mammal, bird or reptile a material comprising a weight gain stimulating amount of an alginate having a M content of at least 80%, wherein said immunostimulating material is (i) a pharmaceutical, veterinary or nutraceutical solid dosage form or liquid formulation, (ii) a solid or liquid food or (iii) a solid or liquid nutritional supplement, and wherein said alginate is derived from *Lessonia* seaweed, *Durvillea* seaweed, or *Laminaria* seaweed, *Ecklonia* seaweed or *Macrocystis* seaweed.

2. The method of claim 1, wherein said alginate is derived from *Durvillea* water extract.

* * * * *